United States Patent
Nicholls et al.

(10) Patent No.: US 9,724,034 B2
(45) Date of Patent: Aug. 8, 2017

(54) SKIN STIMULUS

(75) Inventors: Clive Nicholls, Buckinghamshire (GB);
Timothy Simon Evans, Oxfordshire (GB); Christopher W. Hudson, Oxfordshire (GB)

(73) Assignee: OWEN MUMFORD LIMITED, Oxford (GB)

( * ) Notice: Subject to any disclaimer, the term of this patent is extended or adjusted under 35 U.S.C. 154(b) by 943 days.

(21) Appl. No.: 13/508,742

(22) PCT Filed: Nov. 9, 2010

(86) PCT No.: PCT/GB2010/051861
§ 371 (c)(1),
(2), (4) Date: Jun. 6, 2012

(87) PCT Pub. No.: WO2011/055150
PCT Pub. Date: May 12, 2011

(65) Prior Publication Data
US 2012/0245497 A1    Sep. 27, 2012

(30) Foreign Application Priority Data

Nov. 9, 2009    (GB) .................................. 0919568.6

(51) Int. Cl.
*A61H 7/00*    (2006.01)
*A61B 5/00*    (2006.01)
(Continued)

(52) U.S. Cl.
CPC ........ *A61B 5/15194* (2013.01); *A61B 5/1519* (2013.01); *A61B 5/150022* (2013.01);
(Continued)

(58) Field of Classification Search
CPC .. A61M 5/422; A61B 5/14532; A61B 5/1411; A61B 5/150068; A61B 5/150083;
(Continued)

(56) References Cited

U.S. PATENT DOCUMENTS 4,203,431 A    5/1980 Abura et al.
5,609,577 A *  3/1997 Haber ................. A61M 5/3243
                                                         604/110

(Continued)

FOREIGN PATENT DOCUMENTS

CN    1220132 A    6/1999
CN    1658792 A    8/2005
(Continued)

OTHER PUBLICATIONS

Chung JW, "An experimental study on the use of manual pressure to reduce pain in intramuscular injections", J Clin Nurs, Jul. 2002.*
(Continued)

*Primary Examiner* — Justine Yu
*Assistant Examiner* — Tu Vo
(74) *Attorney, Agent, or Firm* — Young & Thompson (57) ABSTRACT

Skin stimulus arrangements are described for creating a stimulus in the skin in the vicinity of a treatment or wound site to alleviate the perception of pain. First and second textured surfaces are provided for making contact with the skin, with the surfaces being moved to create a stimulus which alleviates the perception of pain. The movement may be linear, rotary or a combination of both, and just a single textured surface may be provided.

27 Claims, 12 Drawing Sheets

(51) Int. Cl.
*A61B 5/151* (2006.01)
*A61H 23/00* (2006.01)
*A61H 39/00* (2006.01)
*A61H 39/04* (2006.01)
*A61H 23/02* (2006.01)
*A61H 39/08* (2006.01)
*A61M 5/42* (2006.01)
*A61B 5/15* (2006.01)

(52) U.S. Cl.
CPC .... *A61B 5/15113* (2013.01); *A61B 5/150114* (2013.01); *A61B 5/15117* (2013.01); *A61B 5/15128* (2013.01); *A61B 5/150137* (2013.01); *A61B 5/150183* (2013.01); *A61B 5/150412* (2013.01); *A61B 5/150503* (2013.01); *A61H 7/00* (2013.01); *A61H 7/005* (2013.01); *A61H 23/00* (2013.01); *A61H 23/006* (2013.01); *A61H 23/02* (2013.01); *A61H 39/00* (2013.01); *A61H 39/04* (2013.01); *A61H 39/08* (2013.01); *A61M 5/422* (2013.01); *A61B 5/150259* (2013.01); *A61H 2201/1692* (2013.01); *A61H 2201/1695* (2013.01)

(58) Field of Classification Search
CPC ............ A61B 5/15142; A61B 5/15186; A61B 5/15146; A61B 5/15188; A61B 17/32093; A61B 17/3417; A61B 17/34; A61B 5/150022; A61H 23/02; A61H 7/005; A61H 7/00; A61H 7/002; A61H 7/003; A61H 7/007; A61H 23/00; A61H 23/004; A61H 23/006; A61H 23/06; A61H 39/00; A61H 39/007; A61H 39/02; A61H 39/04; A61H 39/086; A61H 2201/0153; A61H 2201/0157; A61H 2201/1692
USPC ........ 601/15, 17, 46, 67, 68, 69, 72, 73, 84, 601/89, 92, 134, 135, 136, 137; 606/181–186; 600/583
See application file for complete search history.

(56) References Cited

U.S. PATENT DOCUMENTS

| | | | |
|---|---|---|---|
| 5,843,006 A | 12/1998 | Phillips et al. | |
| 5,964,718 A | 10/1999 | Duchon et al. | |
| 6,015,392 A * | 1/2000 | Douglas et al. ............ | 600/583 |
| 6,740,097 B1 | 5/2004 | Sanchez-Martinez | |
| D496,101 S * | 9/2004 | Davison ...................... | D24/112 |
| 6,793,633 B2 | 9/2004 | Douglas et al. | |
| 6,969,359 B2 | 11/2005 | Duchon et al. | |
| 7,087,068 B1 * | 8/2006 | Marshall ......... A61B 5/150022 600/583 |
| 7,842,060 B2 * | 11/2010 | List ............... | 606/182 |
| 2002/0010406 A1 * | 1/2002 | Douglas et al. ............ | 600/583 |
| 2002/0082521 A1 | 6/2002 | Sharma et al. | |
| 2004/0059256 A1 * | 3/2004 | Perez ........................ | 600/583 |
| 2004/0073140 A1 | 4/2004 | Douglas et al. | |
| 2004/0098010 A1 | 5/2004 | Davison et al. | |
| 2004/0162573 A1 | 8/2004 | Kheiri | |
| 2004/0254599 A1 | 12/2004 | Lipoma et al. | |
| 2005/0010135 A1 | 1/2005 | Fischer et al. | |
| 2005/0177071 A1 * | 8/2005 | Nakayama et al. ......... | 600/583 |
| 2005/0215923 A1 * | 9/2005 | Wiegel ....................... | 600/573 |
| 2006/0089566 A1 | 4/2006 | DeHart | |
| 2006/0217636 A1 * | 9/2006 | Braig et al. ................. | 600/583 |
| 2006/0270998 A1 | 11/2006 | Marti | |
| 2007/0005017 A1 | 1/2007 | Alchas et al. | |
| 2007/0060845 A1 | 3/2007 | Perez | |
| 2007/0093728 A1 | 4/2007 | Douglas et al. | |
| 2007/0156163 A1 | 7/2007 | Davison et al. | |
| 2007/0162063 A1 * | 7/2007 | Marshall .......... A61B 5/150412 606/181 |
| 2008/0077168 A1 * | 3/2008 | Nicholls ............ A61B 5/15142 606/182 |
| 2008/0255483 A1 | 10/2008 | Goldberg | |
| 2009/0004628 A1 | 1/2009 | Knutson | |
| 2010/0268259 A1 * | 10/2010 | Oki et al. .................... | 606/185 |

FOREIGN PATENT DOCUMENTS

| | | |
|---|---|---|
| DE | 199 32 884 C1 | 8/2000 |
| DE | 201 03 026 U1 | 8/2001 |
| DE | 10 2004 025651 A1 | 12/2005 |
| DE | 20 2008 008 992 U1 | 9/2008 |
| EP | 1 493 386 A | 1/2005 |
| EP | 1 535 572 A1 | 6/2005 |
| EP | 1 764 047 A2 | 3/2007 |
| JP | 2002065648 A | 3/2002 |
| JP | 2005046612 A | 2/2005 |
| JP | 2007135786 A | 6/2007 |
| WO | 94/21316 A1 | 9/1994 |
| WO | 01/62150 A1 | 8/2001 |
| WO | 2004021886 A1 | 3/2004 |
| WO | 2004/043526 A1 | 5/2004 |
| WO | 2004/043528 A1 | 5/2004 |
| WO | 2005/035018 A2 | 4/2005 |
| WO | 2006/034324 A2 | 3/2006 |
| WO | 2006/067119 A2 | 6/2006 |
| WO | 2007/099367 A1 | 9/2007 |
| WO | 2009/145920 A1 | 12/2009 |
| WO | 2010/002072 A1 | 1/2010 |

OTHER PUBLICATIONS

Taddio A, "Physical interventions and injection techniques for reducing injection pain during routine childhood immunizations: systematic review of randomized controlled trials and quasi-randomized controlled trials", Clin Ther, Jul. 2009.*
International Search Report, dated Jun. 7, 2011, from corresponding PCT application.
British Search Report, dated Mar. 3, 2010, from corresponding British application.
British Search Report, dated Aug. 10, 2010, from corresponding British application.
British Search Report, dated Aug. 20, 2010, from corresponding British application.
CN Search Report, dated Dec. 19, 2013, from corresponding CN application.
EP Communication dated Aug. 7, 2014, from corresponding EP application.
Japanese Office Action dated Sep. 30, 2014, from corresponding JP application.

* cited by examiner

SKIN STIMULUS

This invention apparatus for creating a skin stimulus in use in order to alleviate the perception of pain in the vicinity of a treatment or wound site on the skin of a human or animal body.

In our earlier publication WO0162150 we describe a skin pricker device having a nose portion with a number of projections that press into the user's skin adjacent to the point to be punctured by the lancet. When the device is pressed against the skin, the projections are felt by the user and this is believed to confuse the nerves in the region of the impending prick so that, when the prick is made, it is less noticeable than it would otherwise be. In this manner the pain normally experienced on pricking the skin is masked so that the perception of pain is alleviated.

The invention therefore relates generally to skin stimulus apparatus for alleviating the perception of pain around a treatment or wound site and more specifically, but not exclusively, to skin penetration devices in which a penetration element penetrates the skin of the user. This may be a momentary penetration such as that of a lancet tip or blade creating an incision, or a needle puncturing the skin for injecting a medicament or taking a sample of body fluid, or a longer term penetration such as the needle of a syringe driver, or a cannula, which is left in the skin of a patient for extended periods.

EP1493386 discloses a lancing device in which a vibration member is provided which vibrates the skin adjacent to the puncture site. The mode and direction of the vibration are not described. The document discloses the use of piezoelectric member, a DC motor or an AC current power source. Each of these arrangements requires the provision of electrical equipment within the device and this gives rise to environmental concerns, not least due to potential obligations under the WEEE regulations for disposal of electrical and electronic equipment.

We have found that the nerve stimulation effect afforded by devices such as those described in our application WO0162150 may be enhanced by providing first and second textured surfaces which move relative to one another so that the stimulus applied to the skin varies with time.

Accordingly, in one aspect, this invention provides a skin stimulus apparatus for creating in use a stimulus in the skin in the vicinity of a treatment or wound site to alleviate the perception of pain, said apparatus comprising:

first and second textured surfaces for contacting the skin, and an arrangement for moving one of the textured surfaces relative to the other to create said stimulus.

In this arrangement the skin receives in combination two different stimuli. This can help alleviate the perception of pain in the area of a treatment or wound site, whether this be a puncture from a needle or cannula, an incision from a blade or tip such as a lancet, or any other site that generates pain, itching or discomfort, such as an insect bite.

In a detailed preferred aspect, this invention provides a skin penetration device comprising:

a body, a penetration element mounted in said body for penetrating the skin of the user, a skin stimulus arrangement for creating in use a stimulus in the skin in the vicinity of an intended penetration site to alleviate the perception of pain, characterised in that said skin stimulus arrangement comprises first and second textured surfaces for contacting the skin, and an arrangement for moving at least one of the textured surfaces relative to the other, thereby to create said stimulus.

Although both surfaces could move, it is convenient for said moving arrangement to move one of said textured surfaces whilst the other remains stationary. A wide range of different motions may be applied, but in one arrangement said moving arrangement may move one said textured surface longitudinally with respect to the other surface in a direction, in use, generally towards to the skin. In this manner the textured surface may be pressed into contact with and/or more firmly against the skin before and/or during said penetration. Also to enhance the alleviation of pain, said moving arrangement may be designed in use to urge said one textured surface against the skin during an initial part of the penetration stroke of said penetration element and, towards the end of the penetration stroke of the penetration element, to apply an impulse to said one textured surface more firmly to press it against the skin. Where the device includes a driver for moving the penetration element through its stroke, said penetration element, or an element that moves therewith during penetration movement, may be designed to create an impact which is transmitted to said one textured surface thereby to provide said impulse. Thus, a part of the penetration element may impact directly or indirectly an element on which the textured surface is formed. A bias means may be associated with or act between said penetration element and said one textured surface.

In addition to or instead of movement towards the skin, said moving arrangement may move at least one of said textured surfaces in use in a direction generally parallel to the skin. Here the relative movement of the first and second textured surfaces may be angular, about an axis generally upstanding from the skin in use. Conveniently the first and second textured surfaces may be generally annular and concentrically arranged about the intended penetration site.

We have discovered also that the perception of pain may be alleviated by angular movement of textured surface without requiring a second textured surface.

Thus in another aspect this invention provides a skin penetration device comprising:

a body, a penetration element mounted in said body for penetrating the skin of the user, a skin stimulus arrangement for creating in use a stimulus in the skin in the vicinity of an intended penetration site to alleviate the perception of pain, characterised in that said skin stimulus arrangement comprises a textured surface for contacting the skin and a moving arrangement for effecting relative angular movement of said textured surface and said body, thereby to create said stimulus.

Although the textured surface could move angularly about other axes such as an axis parallel to the skin, it is preferred that the moving arrangement moves said textured surface angularly in use about an axis generally upstanding from the skin, so that a rotary stimulating effect is applied in a continuous ring around the intended penetration site.

In one alternative, said moving arrangement may include a mechanical stored energy device such as a torsion spring for rotating said one textured surface. This obviates the need for batteries or wiring and so makes disposal less restrictive. Preferably said moving arrangement includes means for manually energising said stored energy device.

In order to apply a compound movement to the textured surface said moving arrangement may be adapted initially to move said one textured surface forwardly to contact the skin in use and thereafter to rotate said one textured surface. Where said moving arrangement includes a latch arrangement for retaining said one textured surface against rotation once said stored energy device has been energised, the said latch arrangement may be released by said forward movement of said one textured surface.

Instead of using a dedicated mechanical stored energy device, where said penetration element includes a drive arrangement for moving the penetration element forwardly to effect penetration, said moving arrangement may comprise a linear to angular transmission arrangement between the penetration element and said one textured surface whereby linear movement of said penetration element in use is accompanied by rotary movement of said one textured surface. The linear to angular transmission arrangement may comprise a cam element associated with one of the penetration element and said one textured surface and a camming surface associated with the other thereof. Conveniently said cam element is associated with the penetration element and the camming surface is associated with said one textured surface.

In a preferred arrangement, said penetration element is carried by a holder that moves longitudinally with the penetration element but which is constrained against angular movement, and said cam element is formed integrally with said holder. The angular movement of the textured surface may be either unidirectional or oscillatory.

In order further to enhance the alleviation of the perception of pain, a device may include a vibratory arrangement for imparting vibration to the textured surface or at least one of said textured surfaces. Said vibratory arrangement may generate vibration mechanically resulting from said movement of said textured surface. In this fashion the drive energy is derived from the movement of the textured surface which is typically derived from the movement of the penetration element of a manually energised spring and so no external electronics is required.

Conveniently, an abutment may be associated with the device body or said textured surface, and cooperate with an interrupted track provided on the other thereof, whereby movement of said textured surface moves said abutment along the interrupted track thereby to impart vibration. The abutment may comprise a resilient member associated with said textured surface.

In another aspect where the penetration element includes a longitudinal portion that moves longitudinally to penetrate the skin, we have found that it is possible to create a stimulus in the skin that can alleviate the perception of pain by contacting the skin with a thin rim or edge closely encircling the intended penetration location.

Accordingly, in a further aspect, this invention provides a skin penetration device comprising:
 a body,
 a penetration element having a longitudinal distal portion with a sharp tip, and mounted in said body for moving longitudinally to a penetrating position in which, in use, it penetrates the skin of the user,
 a skin stimulus arrangement for creating in use a stimulus in the skin in the vicinity of an intended penetration site to alleviate the perception of pain.
 characterised in that said skin stimulus arrangement comprises a nose portion having an aperture through which said tip may pass with clearance, the nose portion having a forwarding facing edge for making edge contact with the skin immediately around the intended penetration site, thereby to create said stimulus.

The nose portion may be of an extended snout shape of tubular form closely surrounding the tip of said penetration element. The wall thickness of said forward facing edge is preferably less than the mean transverse dimension of said aperture. The clearance between the tip and the circumferential wall of the aperture is preferably substantially less than the mean transverse dimension of the tip. The nose region may be stationary relative to the body and simply pressed against the skin by offering up the device to the skin. Alternatively the nose region may be movable and the device may include an arrangement for moving said forward facing edge towards said skin in use as said penetration element moves forwardly. In addition to the edge contact from the nose region, the body or a part thereof may be provided with a textured surface for contacting the skin to provide a further skin stimulus. Thus said nose portion may be movably mounted with respect to said body from a pre-use position in which it lies rearwardly of said textured surface to a forward position in which is it lies alongside or forwardly of said textured surface, and the device may further include a moving arrangement for moving said nose portion forwardly prior to or during said penetration movements to provide a staged or sequential stimulating effect.

In the embodiments above the textured surface may take any suitable form for stimulating a nerve response. For example, said textured surface may include a generally flat base surface from which a plurality of projections extend. The projections may be one or more of conical, cylindrical, rounded, triangular, and saw tooth form. Alternatively said textured surface may comprise a generally flat base surface provided with grooves or relieved portions to leave interrupted skin contact points or surfaces. Still further, the featured surface may be a grained surface.

The skin penetration device may take many forms; for example said penetration element may comprise the needle of a syringe for being inserted into the skin to effect an injection. Alternatively said penetration element may comprise a lancet blade for penetrating the skin by incision. Still further, said penetration element may comprise the needle of an indwelling device designed continuously or intermittently to deliver and/or sample one or more substances to or from the skin.

In another aspect, this invention provides a method for creating a stimulus in the skin in the vicinity of a treatment site to alleviate the perception of pain, which method includes contacting the skin with first and second texture surfaces and moving one of said surfaces relative to the other.

Whilst the invention has been described above, it extends to any inventive combination of the features set out above or in the following description, drawings or claims.

The invention may be performed in various ways and, by way of example only, various embodiments thereof will now be described, reference being made to the accompanying drawings, in which.

Figure 2A:
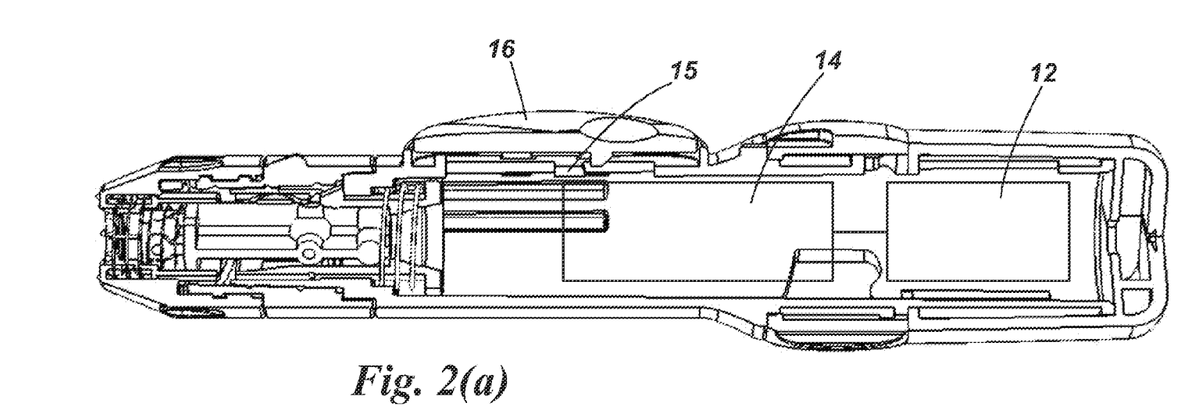
FIGS. 2(a) and 2(b) are full longitudinal sectional views through the lancing device of FIGS. 1(a) and (b) with the confuser ring in the retracted rest position and in the forward position respectively.

The various embodiments of the lancing device illustrated in the drawings comprise an outer housing 10 in the rear part of which is a drive mechanism which includes a drive spring 12, a hammer 14 and a trigger 16, illustrated schematically in FIG. 2(a). The lancing device is cocked by moving the hammer 14 rearwardly against the bias of the spring until it is cocked by a latch 15 on the housing associated with the trigger 16. The hammer may be moved to the cocked position by pulling a rearward housing portion. The construction and operation of such a device is described in detail in our co-pending application US2007156163, the contents of which are incorporated herein by reference.

In the front end of the housing 10 is disposed a lancet holder 18 which is mounted in the housing for limited longitudinal movement and biased rearwardly by a lancet holder spring 20. A disposable lancet 22 having a tip or blade 24 may be introduced into the lancet holder by removing a forward portion of the housing 10 and pushing the lancet 22 into the holder 18. The lancet is typically provided with a safety cap which is twisted off prior to use to expose the tip 24. In use, when the device is fired, the hammer 14 shoots forwardly and impacts the rear end of the lancet holder 18 so that the lancet holder and lancet move forwardly so that the lancet tip 24 projects momentarily beyond the front of the device to make an incision in the skin to draw a bead of blood. The hammer 14 recoils after impact and the lancet holder 18 and lancet 22 retract back into the housing under the influence of the spring 20.

Figure 1A:
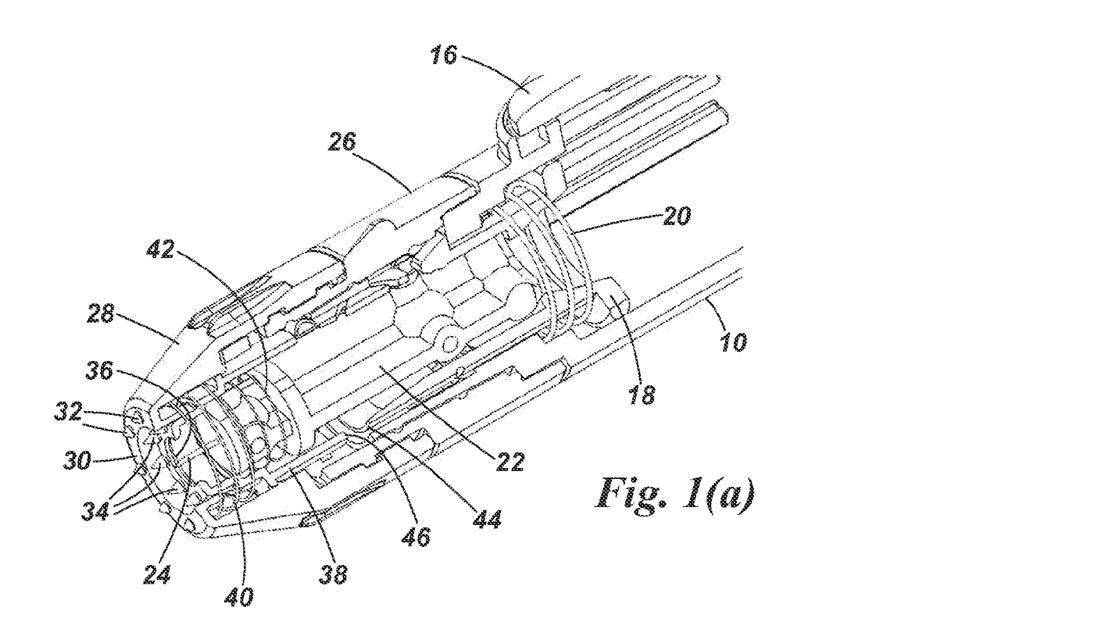
FIGS. 1(a) and 1(b) are part-section front end views of a first embodiment of this invention with the inner, movable confuser ring in the retracted rest position prior to firing of the lancet, and in the forward position respectively.
Figure 1B:
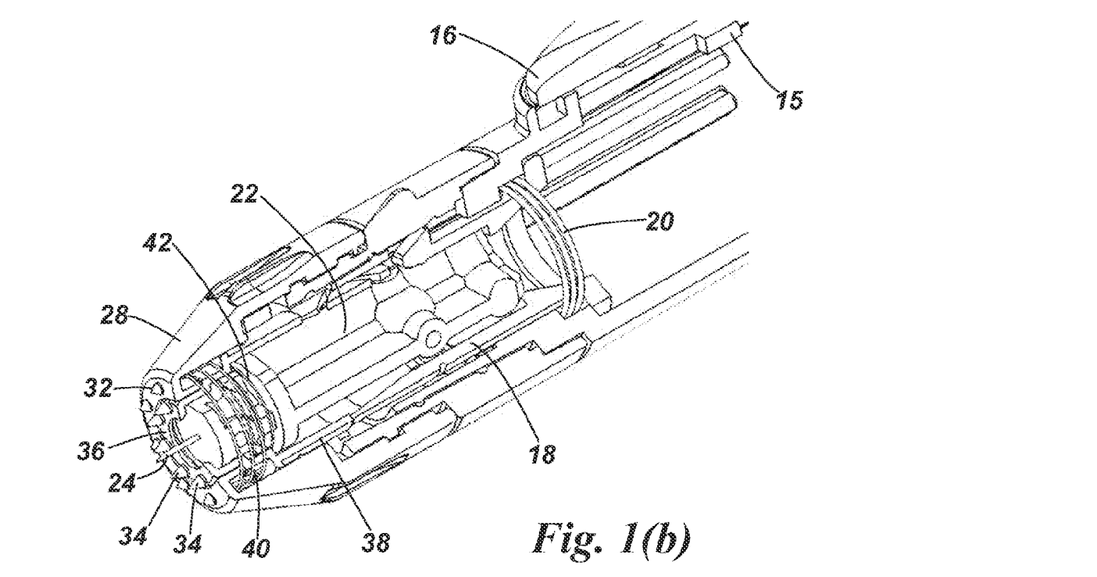
Figure 2B:
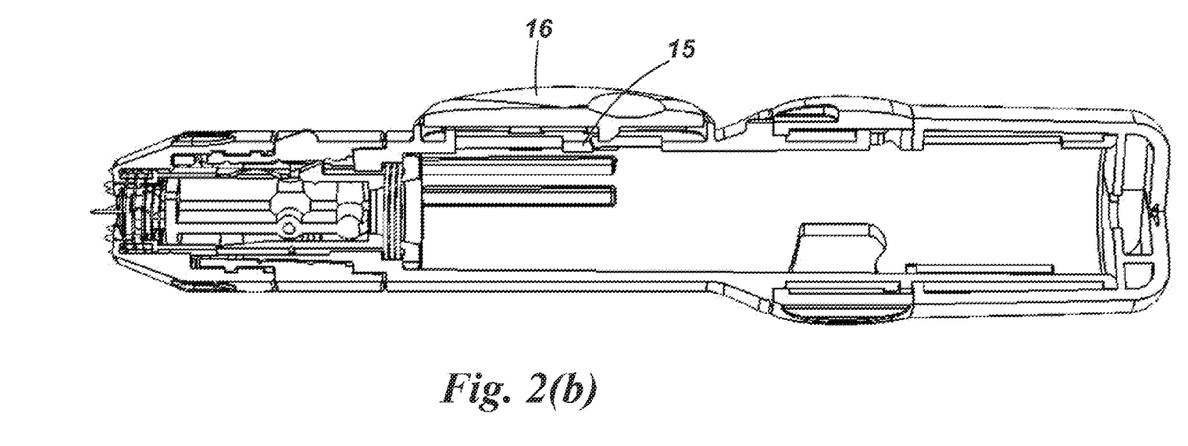
Figure 3A:
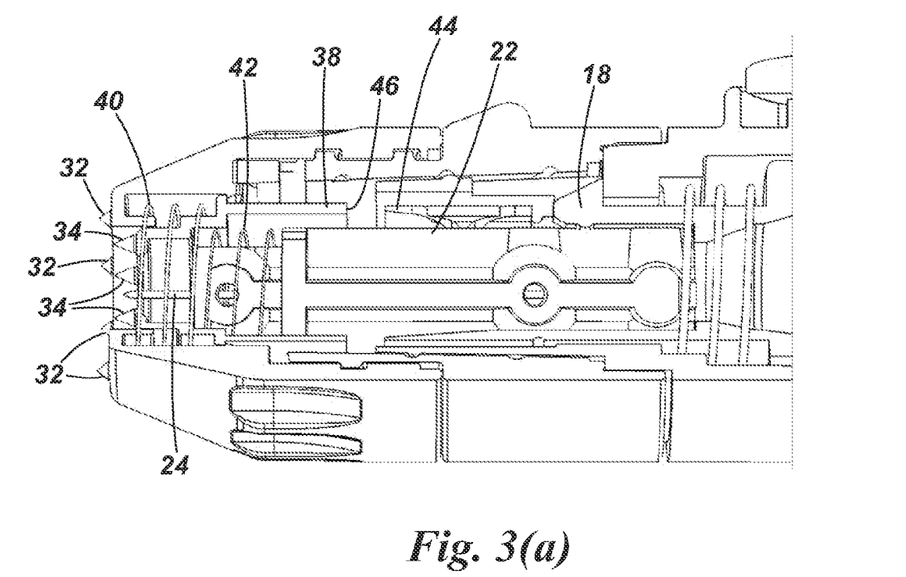
FIGS. 3(a) and 3(b) are respective part-section side views of the embodiment of FIGS. 1 and 2 with the confuser ring in its retracted and forward positions respectively.
Figure 3B:
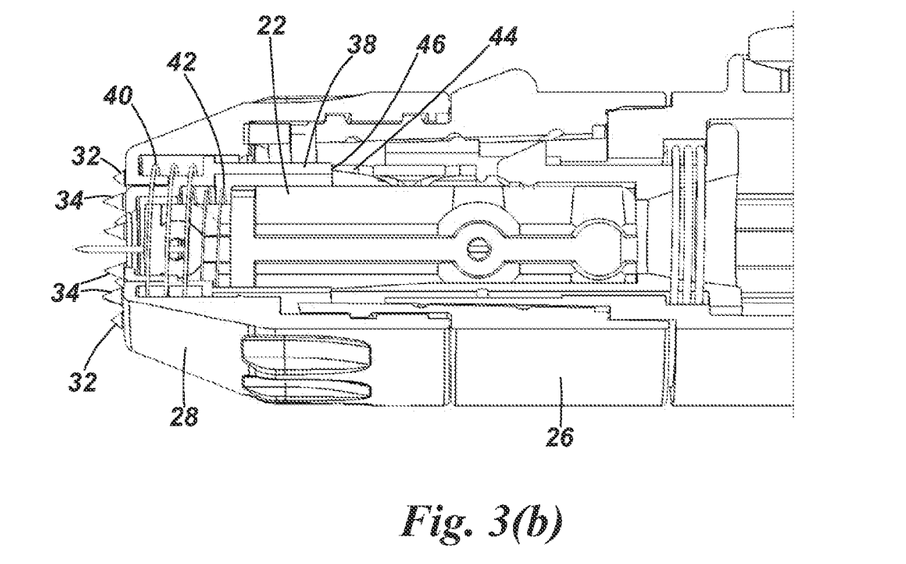

Referring now in more detail to FIGS. 1 to 3, the housing is provided with a removable cap 26 which is screw-threaded onto the front end of the housing and itself carries screw-threaded nose cone 28 to allow a penetration depth to be set by rotating the nose cone 28. The nose cone 28 is provided with an annular flat platform 30 from which project a plurality of projections 32 of conical form. The projections 32 are designed to stimulate the skin so as to 'confuse' the nerve endings and alleviate the perceived pain experienced when the lancet tip penetrates the skin to make an incision. In addition to the fixed annular array of projections 32 a further set of projections 34 is disposed on an annular platform 36 on the front end of a movable confuser ring 38 which is slideably mounted concentrically within the nose cone 28 for movement between the rearward position shown in FIG. 1(a) and the forward position shown in FIG. 1(b). The moveable confuser ring 38 is biased rearwardly by an outer spring 40 acting between the confuser ring 38 and the nose cone 28. A further, stiffer, inner spring 42 is disposed between the front end of the lancet 22 and an inner surface on the confuser ring 38.

In use, prior to firing, the movable confuser ring 38 is in the retracted position shown in FIGS. 1(a), 2(a) and 3(a), biased rearwardly by the spring 42. In this position the front edge 44 of the lancet holder 18 is spaced longitudinally from the rear edge 46 of the movable confuser ring 38. On firing the device, the hammer impacts the rear end of the lancet holder 18 driving the lancet holder 18 and lancet 22 forwardly. As this happens the less stiff spring 40 compresses allowing movement of the confuser ring 38 into its forward position, pushed by the lancet via the spring 42. Once forward movement of the confuser ring 38 is arrested the forward edge 44 of the lancet holder 18 then compresses the stiffer spring 42 and impacts the rearward edge 46 of the movable confuser ring 38. This allows the confuser ring 38 to be driven forwardly to press the projections 35 into the skin. Thus, during a lancing operation the skin adjacent the lancing site is initially contacted by the outer stationary confuser ring projections 32 which provide an initial 'confusing' effect. On firing the lancet, either during or on initial penetration, the projections 35 of the movable confuser ring are forced into contact with the skin and the ring the ring then impacted to induce a mechanical shock to provide a sequential confusing effect. In a simpler alternative, there is no spring 42 and the movable confuser ring 38 is simply driven forward by forward edge 44 so that the second part of the stimulus occurs during needle insertion.

Instead of the movable confuser ring moving axially, it will of course be appreciated that it may instead, or in addition, move angularly, using one or more of the mechanisms described with the embodiments below.

Referring now to the second embodiment shown in FIG. 4, again the drive mechanism comprises a hammer which, when released, impacts on the rear of a lancet holder 118 mounted in the housing 110 and biased rearwardly by a lancet holder spring 120. In this embodiment, a movable confuser ring 138 is designed to shift forwardly and to rotate during the lancing operation so that the projections 134 on the front thereof are pressed axially into the skin and then slid angularly across the surface of the skin around the lancing site in a circle.

The confuser ring 138 is of generally cylindrical form with the forward portion thereof being stepped down in diameter and the rear end thereof carrying a tooth ring portion 150. The confuser ring is biased rearwardly by a return spring 152 acting between an inner forward recess in the housing 110 and the stepped shoulder of the confuser ring 138, to the rearmost position shown in FIG. 4(a). A manually turnable charge ring 154 is rotatably mounted on a forward part of the housing 110 for rotation in one direction only by means of a ratchet arrangement generally indicated at 154a. The charge ring 154 carries an internal toothed ring portion 156 which, when the confuser ring 138 is in its rearmost position of FIG. 4(a) meshes with the toothed portion 150 on the confuser ring. In this manner, twisting the charge ring 154 in the appropriate direction turns the confuser ring 138 against the bias of a torsion spring 160 and holds it there due to ratchet arrangement 154a.

The lancet holder 118 is designed to receive at its forward end a disposable lancet 122 that is loaded into the holder through the aperture 156 in the front end of the confuser ring 138 and which can be ejected therefrom after use by any suitable ejection mechanism. The lancet holder 118 has diametrically opposed transverse lugs 158 that cooperate with a thrust component 159 that comprises at its forward end a thrust collar 162 connected by integrally formed concertina spring arms 164 to thrust pads 166. In the pre-use condition of FIG. 4(a) the concertina arms 164 are fully extended.

Figure 4A:
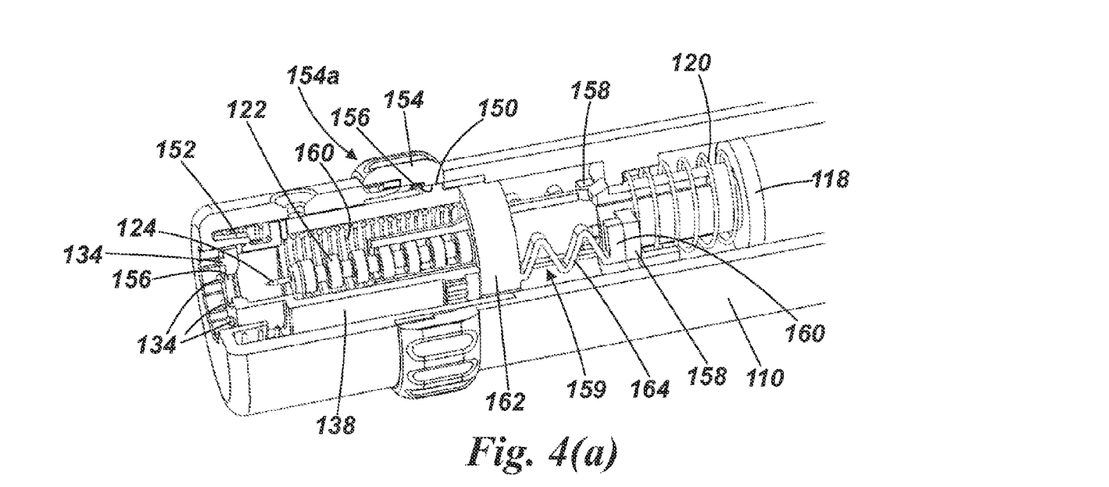
FIGS. 4(a) to 4(f) are respective views of a second embodiment of the lancing device in accordance with the invention, having a linearly and angularly movable confuser ring with mechanically driven vibration.
Figures 4B, 4C:
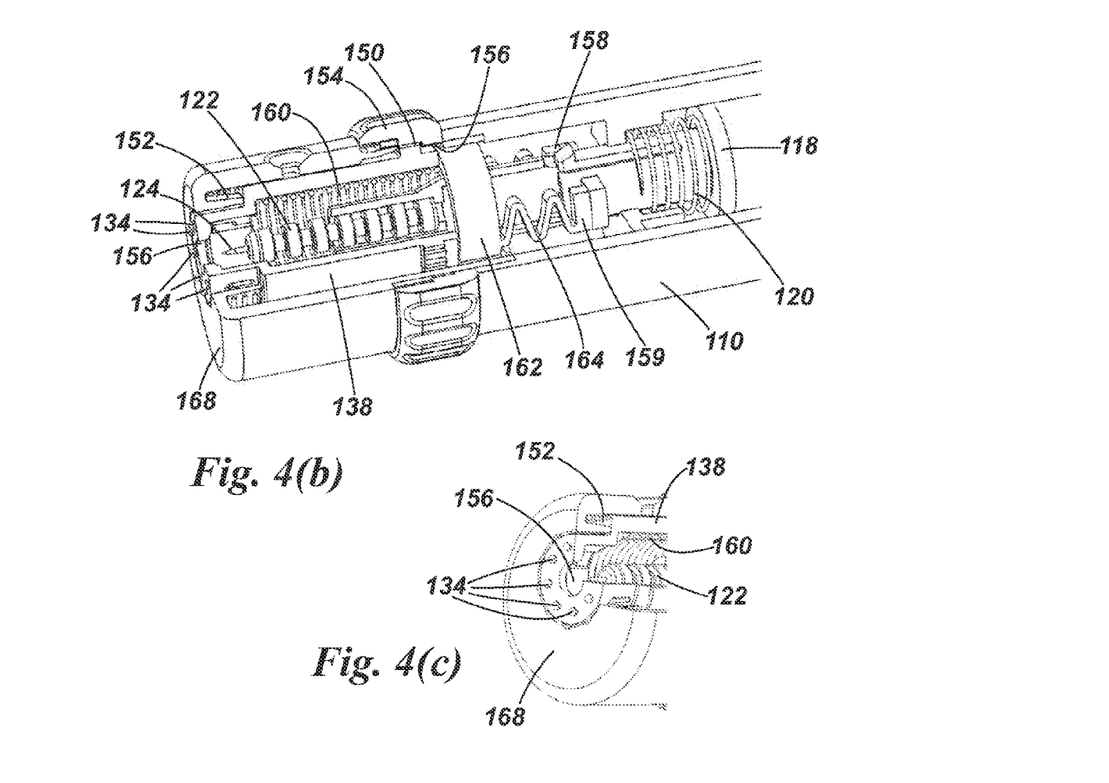

On firing the lancet, the hammer (not shown) impacts the rear end of the lancet holder 118 which moves forwardly carrying the lancet with it. The thrust component 159 is shifted forwardly so that it shifts the confuser ring 138 forwardly against the force of the return spring 152 until the shoulder abuts an internal surface in the housing, where the confuser ring 138 is positioned with the projections 134 projecting forwardly of the front face 168 of the device, so that the projections 134 impinge on the skin to create a stimulus. Moving the confuser ring 138 forwardly also disengages the toothed portion 150 from the toothed portion 156 on the charge ring 154 so that the confuser ring may now rotate under the influence of the torsion spring 160. In this manner the confuser ring 138 executes a compound motion of axial and angular movement immediately prior to and during penetration of the lancet tip 124 into the skin. FIG. 4(b) shows the device during initial forward movement of the lancet holder 118 with the confuser ring 138 just having disengaged from the charge ring 154 and, FIG. 4(c) is a detailed view.

Figure 4D:
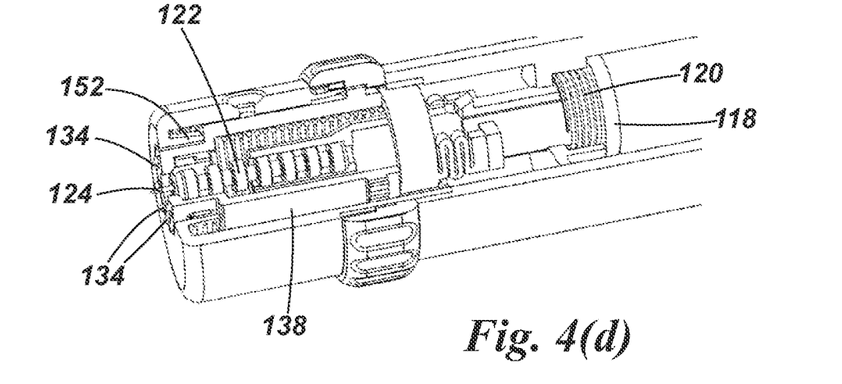

In FIG. 4(d), the lancet holder 118 is at its forwardmost position with the lancet tip penetrating the flesh. Upon recoil of the hammer, the lancet holder 118 returns to its original position under the influence of the spring 120 and the confuser ring 138 is shifted back rearwardly under the influence of the return spring 152.

Figures 4E, 4F:
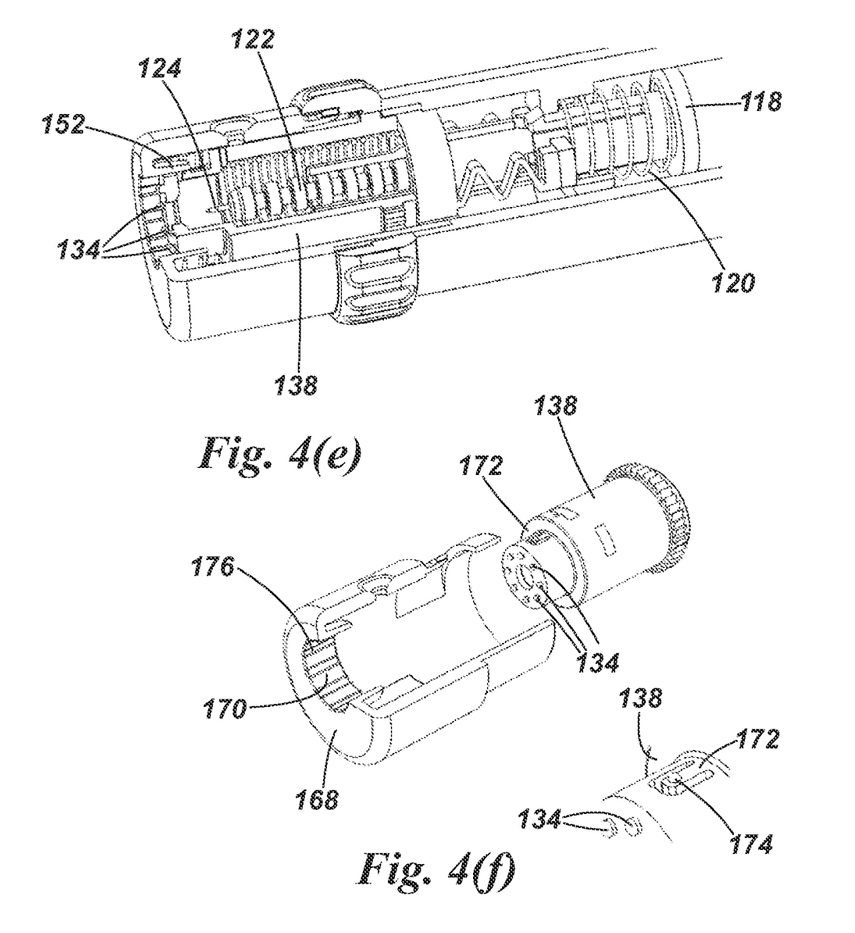

In order to further enhance the confuser effect, the confuser ring 138 and an associated bore 170 in the front end of the housing may be complementarily formed to provide a mechanical vibration as the confuser ring 138 rotates. Thus, as shown in FIG. 4(f), the nerve confuser ring is provided with a flexible beam 172 with a location pip 174 that intermittently locates with longitudinal grooves 176 provided in the bore 170. As the confuser ring 138 rotates, the location pip 174 locates or dislocates with the longitudinal grooves thereby providing a mechanical vibration which may cause additional neural distraction and increase the comfort of needle penetration.

Figure 5A:
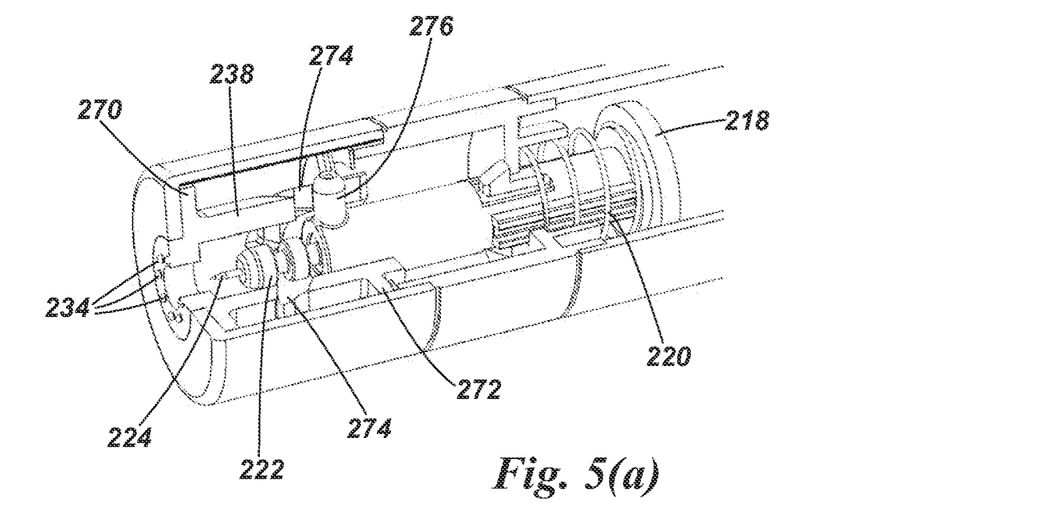
FIGS. 5(a) to 5(h) are views of a third embodiment of lancing device in accordance with this invention having an angularly movable confuser ring with mechanically driven vibration.
Figure 5B:
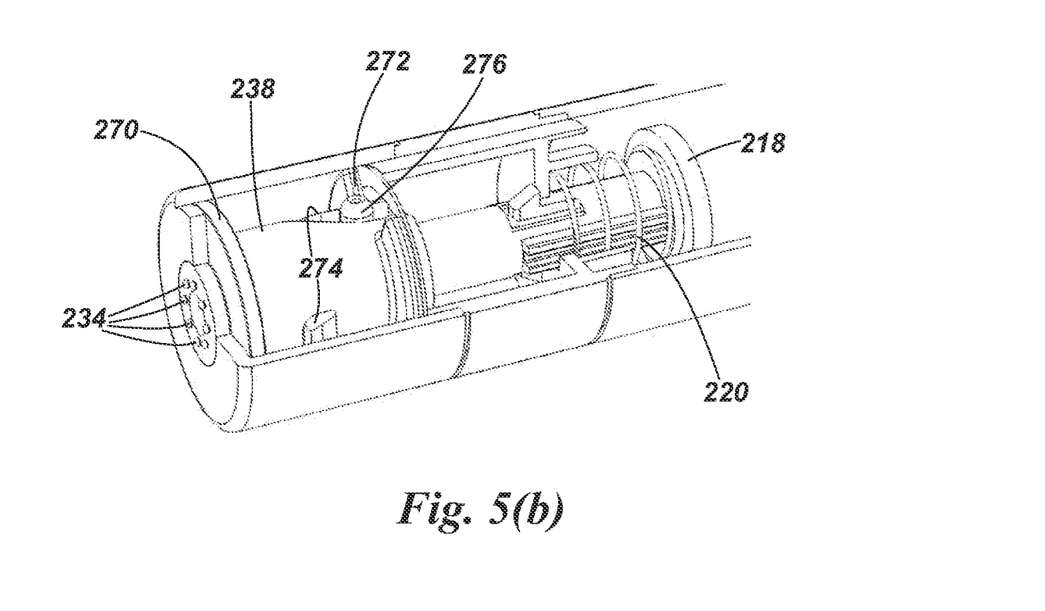
Figure 5C:
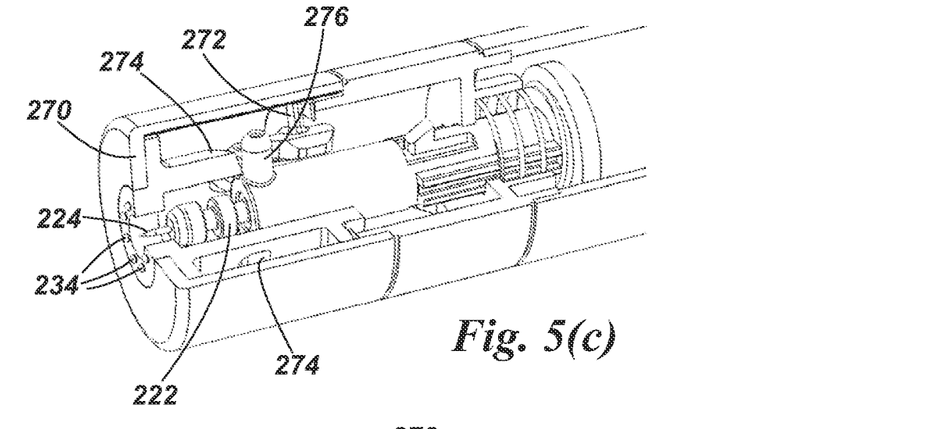
Figure 5D:
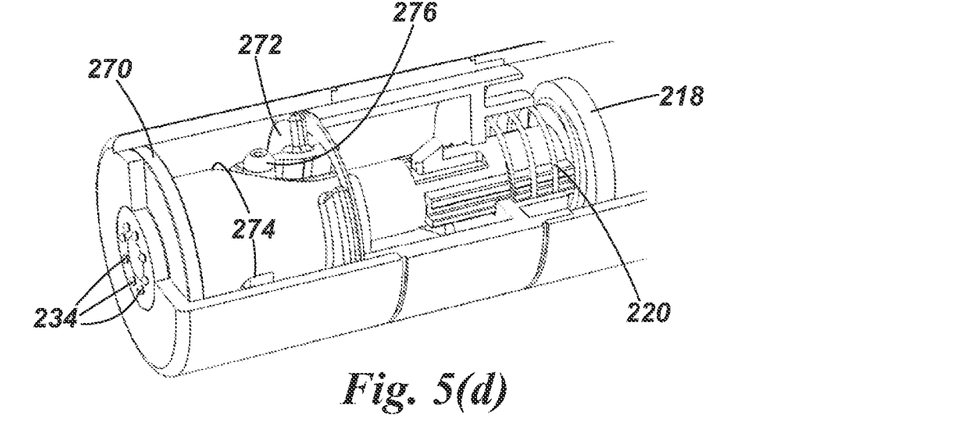
Figure 5E:
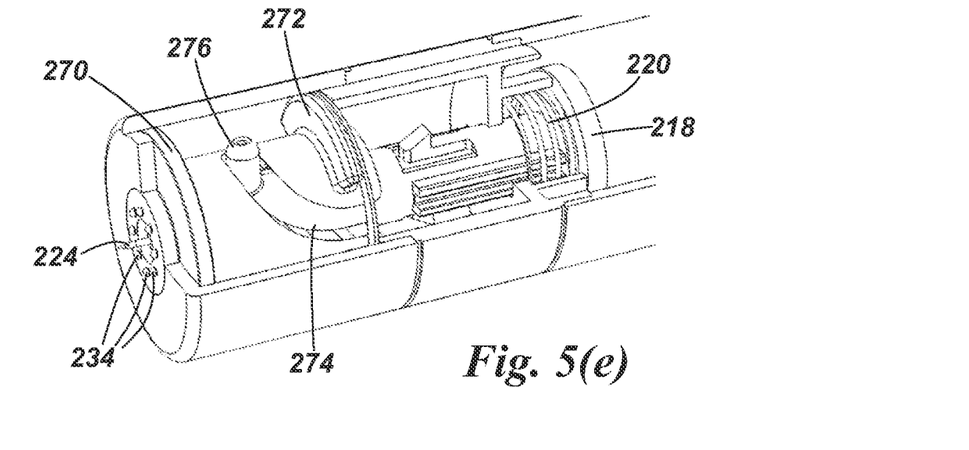
Figure 5F:
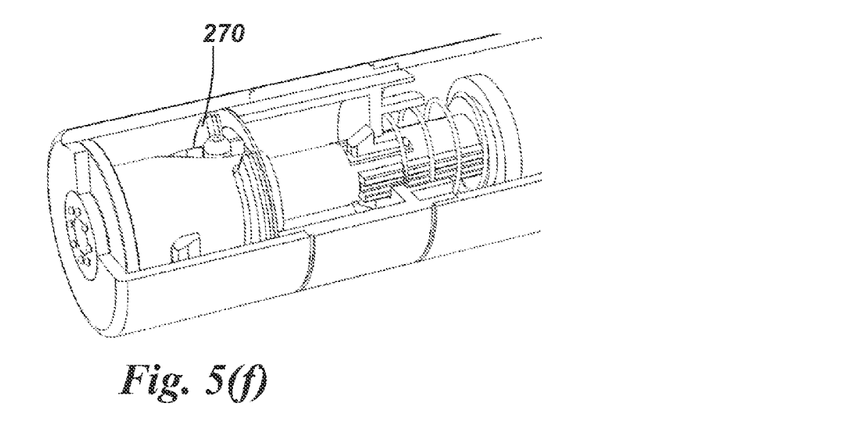
Figure 5G:
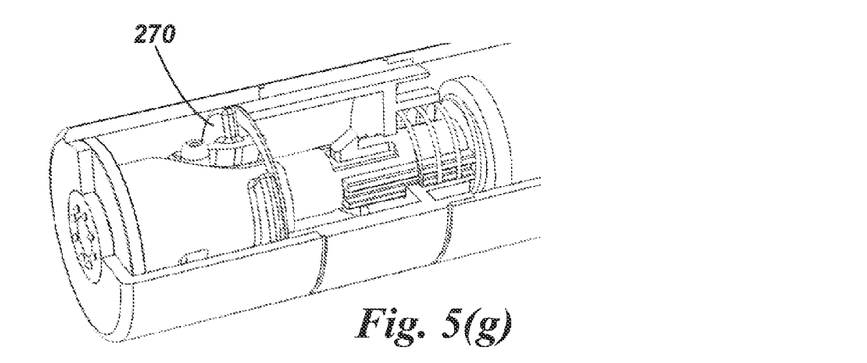

Referring now to FIGS. 5(a) to (h), in this embodiment a rotatable confuser ring 238 is axially fixed but designed to be rotated by movement of the lancet holder, by a camming arrangement. In this arrangement, the confuser ring 238 has a forward flange 270 and a rearward interrupted flange 272 which cooperate with respective opposed surfaces within the housing to prevent axial movement of the confuser ring but to allow rotation thereof. In a cylindrical midportion of the body of the confuser ring 238 are provided diametrically opposed cam slots generally of J-shape with the upper part of the stem of the J open rearwardly. The lancet holder 218 has diametrically opposed drive spigots 276 which run in the slots 274 to cause the confuser ring 238 to rotate in one direction as the lancet moves forwardly and in the reverse direction when the lancet moves rearwardly. FIGS. 5(a) and (b) illustrate the device prior to firing; upon release of the drive mechanism the hammer impacts the lancet holder 218 to drive it forwardly via the position shown in FIGS. 5(c) and (d), where the confuser ring is beginning to turn in one sense immediately before penetration of the lancet tip 224 with this movement continuing as the lancet tip penetrates the skin (FIG. 5(e)). This is reversed as the lancet holder 218 and lancet 222 return to the original position under the influence of lancet holder spring 220 as seen in FIGS. 5(f) and (g).

Figure 5H:
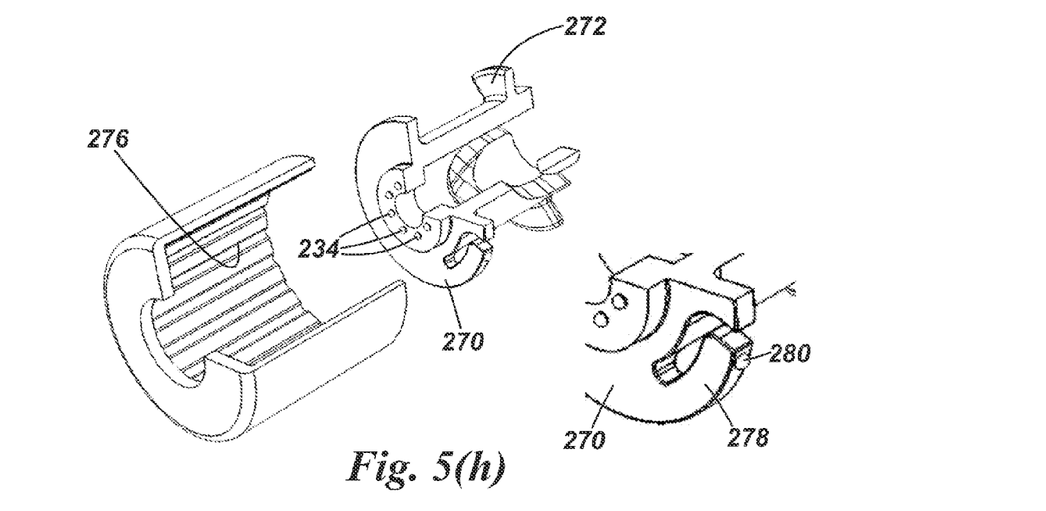
Figure 6A:
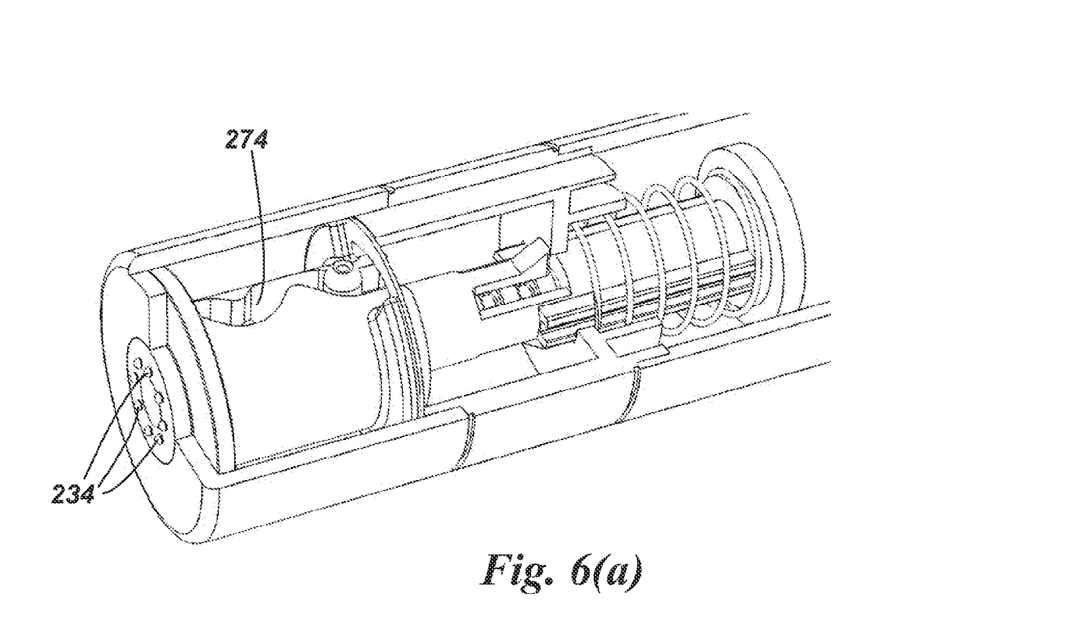
FIGS. 6(a) to 6(e) are views of a fourth embodiment of lancing device in accordance with the invention with an angularly movable confuser ring.
Figure 6B:
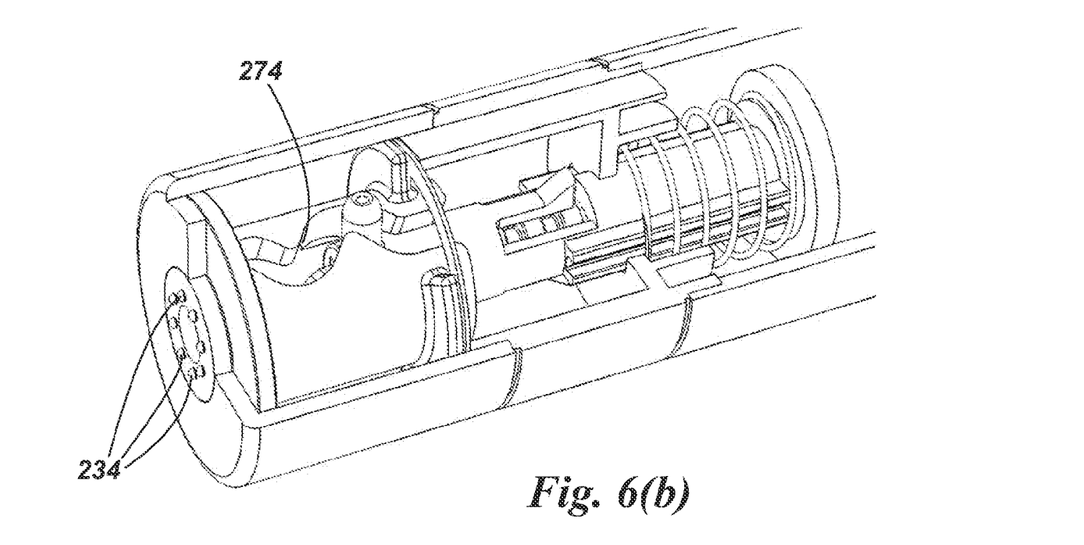
Figure 6C:
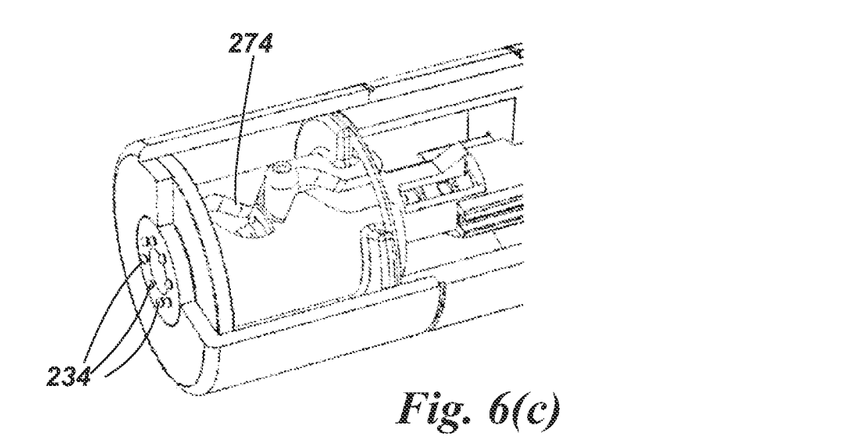
Figure 6D:
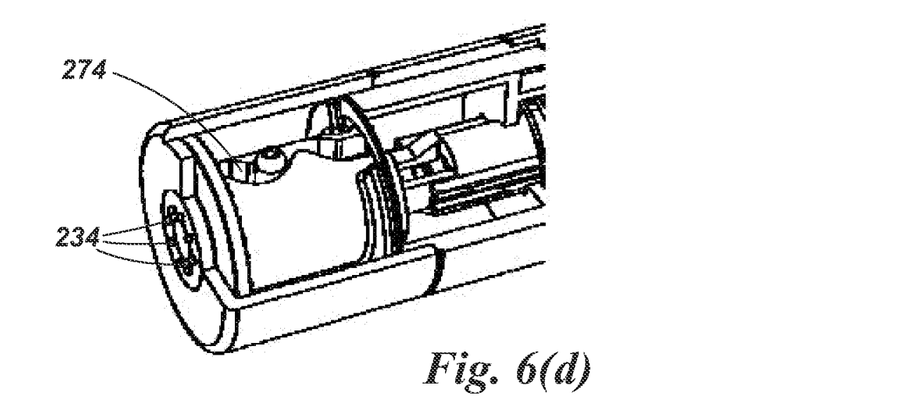
Figure 6E:
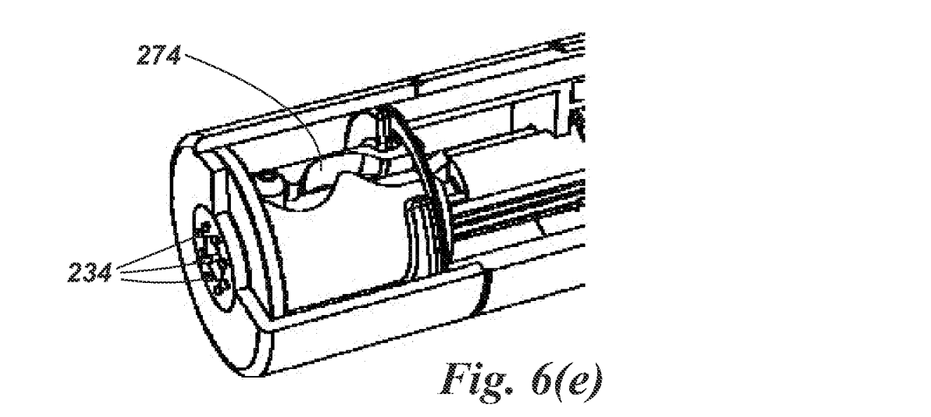

As with the embodiment of FIG. 4, a mechanical vibration arrangement may be provided so that, as the confuser ring 238 rotates, it vibrates to provide further nerve confusion. As shown in FIG. 5(h), the forward flange 270 may be provided with a flexible beam 278 with a location pip 280 that intermittently locates with longitudinal grooves 276 in a forward part of the housing.

Referring now to the embodiment of FIG. 6, this is similar to that of FIG. 5 except the profile of the cam slot 274 is of undulating serpentine form rather than the J-shape. Thus, as the lancet advances towards the skin the confuser ring 138 executes an oscillatory motion.

It will of course be appreciated that, the embodiments of FIGS. 4 to 6 could be provided with a stationary textured surface on the skin-contacting end face of the front cap surrounding the confuser ring.

Figure 7A:
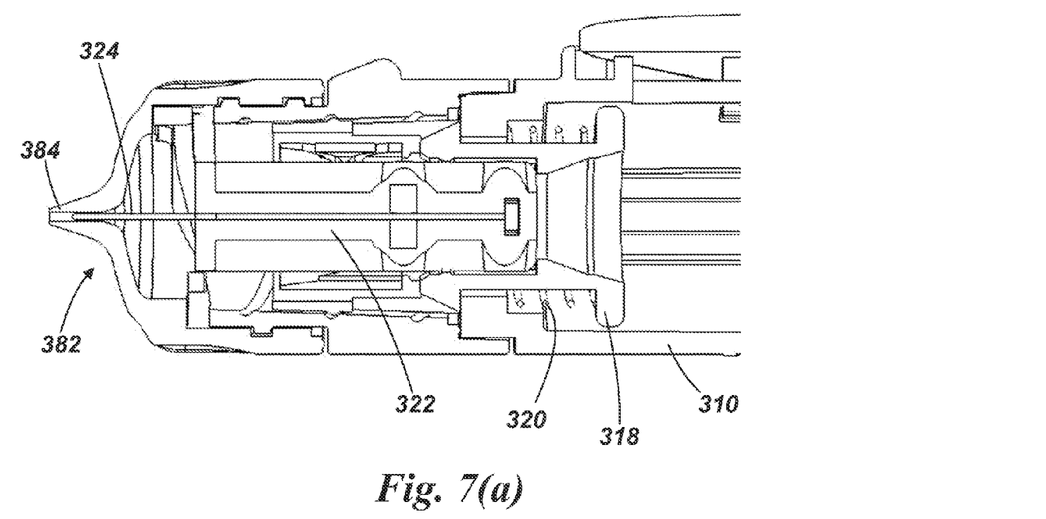
FIGS. 7(a) and 7(b) are views of a fifth embodiment of lancing device in accordance with this invention with a small diameter edge contact confuser ring axially fixed with respect to the body of the lancing device.
Figure 7B:
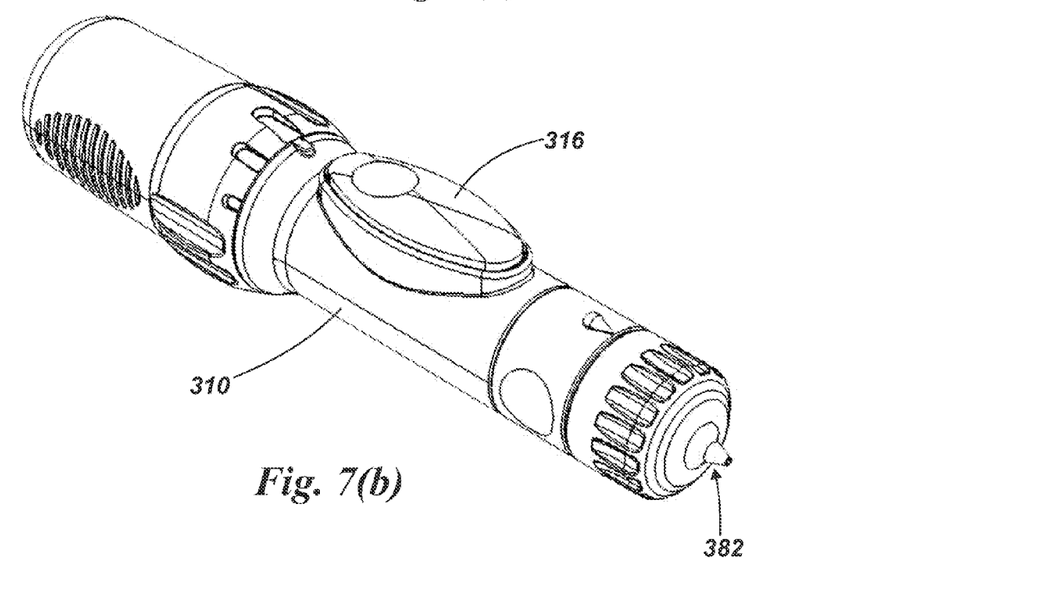

Referring now to the embodiments shown in FIGS. 7(a) and (b), here the device has housing 310, trigger 316, lancet holder 318, lancet holder spring 320, lancet 322 and a nose with a hollow spike or snout 382 having a narrow bore 384 through which the tip 324 of the lancet 322 projects.

Compared to existing lancing devices which usually have a flat end face providing broad annular extended surface contact with the skin around the penetration site, in the embodiment of FIGS. 7(a) and (b), there is edge contact only, immediately around the injection site, which approximates to line contact. We have found that providing edge or line contact immediately around the penetration site provides a nerve confusion effect alleviating the pain.

Figure 8A:
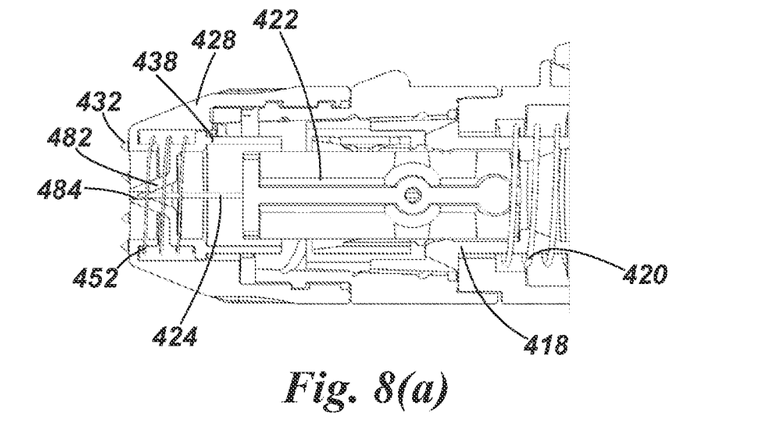
FIGS. 8(a) to 8(c) are views of a sixth embodiment of lancing device in accordance with this invention having an outer annular fixed confuser ring with a plurality of projections and an inner small diameter movable confuser ring.
Figure 8B:
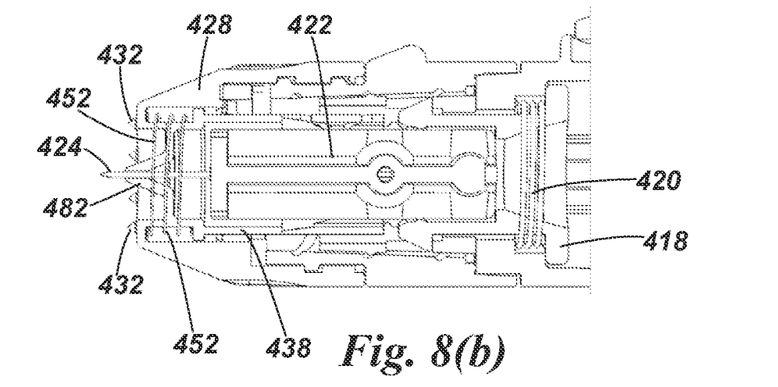
Figure 8C:
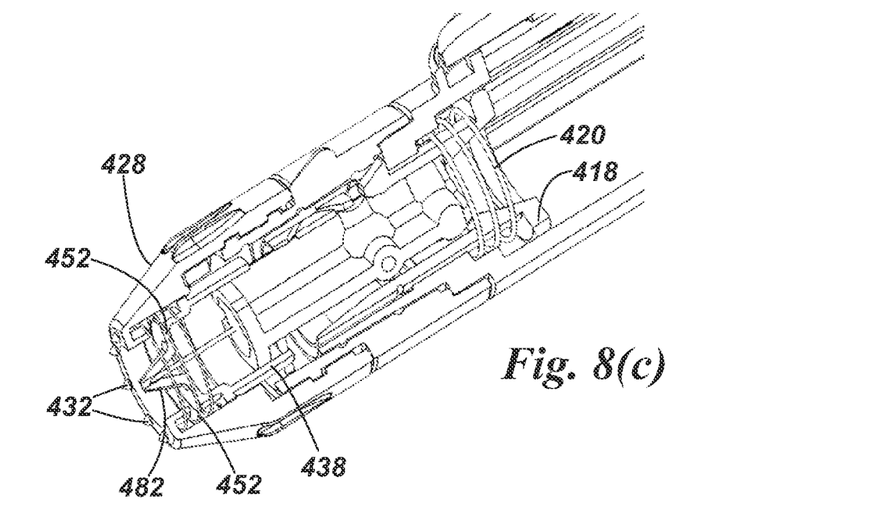

Referring now to the embodiment of FIG. 8, in this arrangement a movable confuser ring 438 is provided with a profile similar to that of the nose portion of the embodiment of FIG. 8, having a hollow spike or snout portion 482 with an aperture 484 closely surrounding the tip 424 of the lancet 422. The confuser ring 438 is capable of limited longitudinal movement to the position shown in FIG. 8(a) and that shown in FIG. 8(b) against the influence of a return spring 452. In this embodiment the nose cone 428 has a flat annular surface from which project an outer circle of static projections 432. In this arrangement, when the lancing device is offered up to the skin the projections 432 make initial skin contact and provide nerve confusion signals. Upon firing the lancet, the lancet holder moves forward and pushes the confuser ring 438 forward so that the hollow spiked portion thereof impinges and presses against the skin to provide further nerve confusion prior to or as the lancet tip 424 penetrates the skin. As the lancet holder 418 returns to its original position under the influence of spring 420, the confuser ring 438 is returned to its initial position by the return spring 452.

The invention claimed is:
1. A skin penetration device comprising:
   a body (10), a penetration element (22) mounted in said body for penetrating the skin of the user,
   a skin stimulus arrangement for creating a stimulus in the skin in the vicinity of an intended penetration site to alleviate the perception of pain,
   wherein said skin stimulus arrangement comprises first and second textured surfaces (30, 36), for contacting the skin,
   the first textured surface comprising a flat annular surface surrounding an aperture, through which the penetration element projects in use, and an array of projections extending from the flat annular surface and surrounding the aperture, and the second textured surface comprising a flat annular surface surrounding the aperture, through which the penetration element projects in use, and an array of projections extending from the flat annular surface and surround the aperture, the first and second textured surfaces being arranged concentrically around an axis of the aperture and an arrangement (18, 44, 46) configured for moving at least one of the textured surfaces relative to the other, thereby to create said stimulus, wherein the axis of the aperture is normal to the flat annular surface, and moving at least one of said textured surfaces relative to the other comprises an angular movement around the axis of the aperture.

2. The skin penetration device according to claim 1, wherein the first textured surface is an outer surface and the second textured surface is an inner surface, said moving arrangement (18, 44, 46) is adapted to move the second textured surface (36) whilst the first textured surface remains stationary (30).

3. The skin penetration device according to claim 2, wherein said moving arrangement (18, 44, 46) is configured to move said second textured surface (36) longitudinally with respect to the first surface (30) in a direction, when in use, generally towards the skin.

4. The skin penetration device according to claim 3, wherein said moving arrangement (18, 44, 46) is configured to urge said second textured surface (36) against the skin during an initial part of the penetration stroke of said penetration element and, towards the end of the penetration stroke of the penetration element, to apply an impulse to said second textured surface more firmly to press it against the skin.

5. The skin penetration device according to claim 4 including a driver means (12) for moving the penetration element (22) through its stroke and, wherein said penetration element, or an element (44) that moves therewith during penetration movement, is adapted to create an impact which is transmitted to said one textured surface thereby to provide said impulse.

6. The skin penetration device according to claim 4, wherein said moving arrangement (18, 44, 46) includes bias means (40) associated with or acting between said penetration element and said second textured surface (36).

7. The skin penetration device according to claim 1, wherein said moving arrangement (18, 44, 46) is configured to move at least one of said textured surfaces (36), when in use, in a plane generally parallel to a location on the skin at which the penetration element is intended to penetrate.

8. The skin penetration device according to claim 1, wherein the first and second textured surfaces (30, 36) are generally annular and concentrically arranged about the intended penetration site, the first textured surface being an outer annular surface and the second textured surface being an inner annular surface.

9. The skin penetration device according to claim 1, wherein said moving arrangement (118, 158, 159, 160) includes a stored energy device (160) for rotating said at least one of the textured surfaces.

10. The skin penetration device according to claim 9, wherein said stored energy device (160) is a torsion spring.

11. The skin penetration device according to claim 9, wherein said moving arrangement (118, 158, 159, 160) includes means (152) for manually energizing said stored energy device (160) for rotating said at least one of the textured surfaces.

12. The skin penetration device according to claim 9, wherein said moving arrangement (118, 158, 159, 160) is adapted initially to move said at least one of the textured surfaces (138) forwardly to contact the skin in use and thereafter to rotate said at least one of the textured surfaces about an axis generally normal to the skin.

13. The skin penetration device according to claim 12, wherein said moving arrangement (118, 158, 159, 160) includes a latch arrangement (150, 156) for retaining said at least one of the textured surfaces (138) against rotation once said stored energy device (160) has been energized, and said latch arrangement is released by said forward movement of said at least one of the textured surfaces.

14. The skin penetration device according to claim 1, wherein said penetration element (22; 122) includes a drive arrangement for moving the penetration element forwardly to effect penetration, and said drive arrangement comprises a linear to angular transmission arrangement (274, 276) between the penetration element and said at least one of the textured surfaces whereby linear movement of said penetration element in use is accompanied by rotary movement of said at least one of the textured surfaces.

15. The skin penetration device according to claim 14, wherein said linear to angular transmission arrangement comprises a cam element (276) associated with one of the penetration element (122) and one of the textured surfaces (138) and a camming surface (274) associated with the other textured surface.

16. The skin penetration device according to claim 15, wherein said cam element (276) is associated with the penetration element (122) and the camming surface (274) is associated with said at least one of the textured surfaces (138).

17. The skin penetration device according to claim 16, wherein said penetration element (122) is carried by a holder (218) that moves longitudinally with the penetration element but which is constrained against angular movement, and said cam element (276) is formed integrally with said holder.

18. The skin penetration device according to claim 1, wherein said angular movement is unidirectional.

19. The penetration device according to claim 1, wherein said angular movement is oscillatory.

20. The skin penetration device according to claim 1, including a vibratory arrangement (170, 172; 276, 280) for imparting vibration to at least one of said textured surfaces.

21. The skin penetration device according to claim 20, wherein said vibratory arrangement (170, 172; 276, 280) generates vibration mechanically in response to said movement of said at least one of the textured surfaces.

22. The skin penetration device according to claim 21, including an abutment (172, 280) associated with one of said device body and one of the textured surfaces, in cooperation with an interrupted track (170, 276), which is provided with a plurality of interruptions spaced along the length of the track, provided on the other textured surface, whereby movement of said one of the textured surfaces moves said abutment along the length of the track such that the plurality of the interruptions spaced along the track thereby to impart vibration to the textured surface as the abutment travels over the interruptions along the track.

23. The skin penetration device according to claim 22, wherein said abutment comprises a resilient member associated with said one of the textured surfaces.

24. The skin penetration device according to claim 1, wherein said projections comprise one or more of conical, cylindrical, rounded, triangular, and saw tooth projections.

25. The skin penetration device according to claim 1, wherein said penetration element comprises the needle of a syringe for being inserted into the skin to effect an injection.

26. The skin penetration device according to claim 1, wherein said penetration element comprises a lancet blade for penetrating the skin by incision.

27. A skin penetration device comprising:
- a body (10; 110),
- a penetration element (22; 122) mounted in said body for penetrating the skin of the user,
- a skin stimulus arrangement for creating in use a stimulus in the skin in the vicinity of an intended penetration site to alleviate the perception of pain,
- wherein said skin stimulus arrangement comprises a first textured surface having a flat annular surface surrounding an aperture and second textured surface for contacting the skin and a moving arrangement (118, 158, 159, 160) for effecting relative angular movement of said second textured surface and said body, when in use, thereby to create said stimulus, wherein, the first and second textured surfaces are arranged concentrically around an axis of the aperture, and wherein the axis of the aperture is normal to the flat annular surface and moving said second textured surface relative to the first texture surface comprises an angular movement around the axis of the aperture.

* * * * *